United States Patent
Dhawan et al.

(10) Patent No.: US 12,195,371 B2
(45) Date of Patent: Jan. 14, 2025

(54) ANTIFOULING COMPOUNDS USED FOR MICROBIAL FOULING CONTROL

(71) Applicant: Ecolab USA Inc., St. Paul, MN (US)

(72) Inventors: Ashish Dhawan, Aurora, IL (US); Kun Xiong, Naperville, IL (US); Carter Martin Silvernail, Lakeville, MN (US)

(73) Assignee: Ecolab USA Inc., St. Paul, MN (US)

( * ) Notice: Subject to any disclaimer, the term of this patent is extended or adjusted under 35 U.S.C. 154(b) by 222 days.

(21) Appl. No.: 17/338,000

(22) Filed: Jun. 3, 2021

(65) Prior Publication Data
US 2021/0380440 A1  Dec. 9, 2021

Related U.S. Application Data

(60) Provisional application No. 63/034,274, filed on Jun. 3, 2020.

(51) Int. Cl.
| | |
|---|---|
| C02F 1/50 | (2023.01) |
| A01N 31/08 | (2006.01) |
| C07C 43/11 | (2006.01) |
| C08G 65/26 | (2006.01) |

(52) U.S. Cl.
CPC .............. *C02F 1/50* (2013.01); *A01N 31/08* (2013.01); *C07C 43/11* (2013.01); *C08G 65/2612* (2013.01); *C02F 2303/04* (2013.01); *C02F 2303/08* (2013.01); *C02F 2303/20* (2013.01)

(58) Field of Classification Search
CPC .... C02F 1/50; C02F 2303/04; C02F 2303/08; C02F 2303/20; A01N 31/08; A01N 31/14; C07C 43/11; C07C 43/23; C08G 65/2612; C08G 65/22; C09D 171/02
See application file for complete search history.

(56) References Cited

U.S. PATENT DOCUMENTS

| | | | |
|---|---|---|---|
| 2,415,009 | A | 1/1947 | Hatch et al. |
| 2,797,152 | A | 6/1957 | Hughes et al. |
| 3,000,852 | A | 9/1961 | Merz |
| 3,472,666 | A | 10/1969 | Foroulis |
| 3,728,281 | A | 4/1973 | Marks et al. |
| 4,148,772 | A | 4/1979 | Marchetti et al. |
| 4,374,965 | A | 2/1983 | Dickie et al. |
| 4,386,939 | A | 6/1983 | Lange |
| 4,655,287 | A | 4/1987 | Wu |
| 4,664,811 | A | 5/1987 | Operhofer |
| 4,728,497 | A | 3/1988 | Muccitelli |
| 4,770,790 | A | 9/1988 | Oberhofer |

(Continued)

FOREIGN PATENT DOCUMENTS

| | | |
|---|---|---|
| DE | 2348576 A1 | 4/1975 |
| EP | 1777288 B1 | 7/2009 |

(Continued)

OTHER PUBLICATIONS

Arukula, Ravi et al., Investigations on anticorrosive, thermal, and mechanical properties of conducting polyurethanes with tetraaniline pendent groups, Polymers for Advanced Technologies (2018), 29, pp. 1620-1631.
Liu, J. Z. et al., Aryl Aminoalcohols as Corrosion Inhibitors for Carbon Steel in Chloride-Contaminated Simulated Concrete Pore Solution, Int. J. Electrochem. Sci., 11 (2016) pp. 1135-1151.
Mohamed Heba A. et al., Aromatic Amine-Epoxidized Sunflower Free-Fatty-Acid Adducts as Corrosion Inhibitors in Epoxy-Curable Varnishes, Journal of Applied Polymer Science, vol. 124, (2012), pp. 2007-2015.
Ekblad, Tobias et al., Poly(ethylene glycol)-Containing Hydrogel Surfaces for Antifouling Applications in Marine and Freshwater Environments, Biomacromolecules 2008, 9, pp. 2775-2783.
Falk, Nancy A., Surfactants as Antimicrobials: A Brief Overview of Microbial Interfacial Chemistry and Surfactant Antimicrobial Activity, J. Surfact Deterg (2019) 22, pp. 1119-1127.

(Continued)

*Primary Examiner* — Monica A Shin
(74) *Attorney, Agent, or Firm* — Stinson LLP

(57) ABSTRACT

Disclosed herein are antifouling compositions and uses of antifouling compositions for controlling microbial fouling in a system in contact with an aqueous medium. The antifouling compositions comprising an antifouling compound of Formula 1

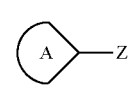

(1)

wherein A is an optionally substituted phenyl, naphthalene, indole, purine, pyridine, quinoline, isoquinoline, pyrimidine, pyrrole, furan, thiophene, imidazole, or thiazole; and Z has the following structure:

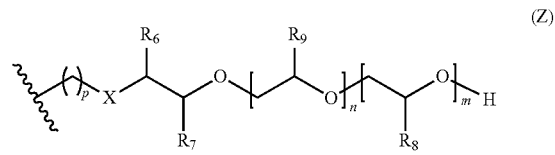

(Z)

wherein X is —O—, —N($R_{10}$)—, —OC(O)—, —C(O)O—, —N($R_{10}$)C(O)—, —C(O)N($R_{10}$)—, —OC(O)O—, —OC(O)N($R_{10}$)—, —N($R_{10}$)C(O)O—, or —N($R_{10}$)C(O)N($R_{10}$)—; p is an integer from 0 to 10; $R_6$ is hydrogen, alkyl, or aryl; $R_7$ is alkyl, aryl, or —($CH_2$)z-O—$R_{11}$; $R_8$ and $R_9$ are independently hydrogen, alkyl or aryl; $R_{10}$ is hydrogen or alkyl; $R_{11}$ is hydrogen or alkyl; m is independently an integer from 2 to 20; n is independently an integer from 3 to 20; and z is an integer from 1 to 10, wherein at least one of $R_8$ and $R_9$ are other than hydrogen and wherein the antifouling composition reduces biofilm growth in a system comprising an aqueous medium.

16 Claims, No Drawings

(56) References Cited

U.S. PATENT DOCUMENTS

| | | |
|---|---|---|
| 4,808,441 A | 2/1989 | Chattha et al. |
| 4,851,421 A * | 7/1989 | Iwasaki ............... A01N 25/14 |
| | | 514/952 |
| 5,057,556 A | 10/1991 | Redman |
| 5,318,805 A | 6/1994 | Wu |
| 5,344,674 A | 9/1994 | Wu |
| 5,380,781 A | 1/1995 | Kato et al. |
| 5,447,974 A | 9/1995 | Peng |
| 5,503,836 A | 4/1996 | Fellers et al. |
| 5,756,221 A | 5/1998 | Horibe et al. |
| 5,770,549 A | 6/1998 | Gross |
| 5,853,462 A | 12/1998 | Spellane et al. |
| 5,876,514 A | 3/1999 | Rolando et al. |
| 5,906,864 A | 5/1999 | Osterhold et al. |
| 6,096,225 A | 8/2000 | Yang et al. |
| 6,120,705 A | 9/2000 | Spellane et al. |
| 6,139,830 A | 10/2000 | Donlan et al. |
| 6,207,731 B1 | 3/2001 | Gam |
| 6,653,370 B2 | 11/2003 | Paar et al. |
| 6,670,041 B2 | 12/2003 | Paar et al. |
| 6,835,459 B2 | 12/2004 | Lorenz et al. |
| 6,911,490 B2 | 6/2005 | Feola et al. |
| 7,141,538 B2 | 11/2006 | Noguchi et al. |
| 7,165,561 B2 | 1/2007 | Baldridge et al. |
| 7,414,162 B2 | 8/2008 | Link et al. |
| 7,470,755 B2 | 12/2008 | Abrami et al. |
| 8,445,585 B2 | 5/2013 | Paar et al. |
| 8,501,997 B2 | 8/2013 | Vedage et al. |
| 8,512,594 B2 | 8/2013 | Walker et al. |
| 8,809,392 B2 | 8/2014 | Li et al. |
| 8,901,063 B2 | 12/2014 | Soontravanich et al. |
| 8,927,479 B2 | 1/2015 | Perlas |
| 9,522,974 B2 | 12/2016 | Barriau et al. |
| 9,663,431 B2 | 5/2017 | Griese et al. |
| 9,670,433 B1 | 6/2017 | Hodge et al. |
| 9,719,057 B2 | 8/2017 | Nielsen et al. |
| 9,809,719 B2 | 11/2017 | Paar et al. |
| 9,850,388 B2 | 12/2017 | Paar et al. |
| 9,889,466 B2 | 2/2018 | Grabbe et al. |
| 10,266,794 B2 | 4/2019 | Hunt, Jr. et al. |
| 10,273,433 B2 | 4/2019 | Man et al. |
| 10,308,886 B2 | 6/2019 | Rana et al. |
| 10,351,801 B2 | 7/2019 | Martinez-Crowley et al. |
| 10,479,959 B2 | 11/2019 | Creamer et al. |
| 2003/0096725 A1 * | 5/2003 | Tsibouklis ............... C11D 3/50 |
| | | 510/505 |
| 2003/0173302 A1 | 9/2003 | Xiong et al. |
| 2008/0108539 A1 * | 5/2008 | Kany ................... C11D 1/78 |
| | | 510/401 |
| 2009/0166291 A1 | 7/2009 | Jackson |
| 2009/0270566 A1 | 10/2009 | Thorman et al. |
| 2011/0071069 A1 | 3/2011 | Konishi et al. |
| 2012/0232169 A1 | 9/2012 | Wu et al. |
| 2013/0126113 A1 | 5/2013 | Tan et al. |
| 2015/0080282 A1 | 3/2015 | Krishna et al. |
| 2018/0163020 A1 * | 6/2018 | Zong ..................... C02F 5/12 |
| 2018/0223112 A1 | 8/2018 | Jaquess |
| 2018/0355284 A1 | 12/2018 | Bhole et al. |
| 2019/0144314 A1 | 5/2019 | Lin et al. |
| 2019/0177661 A1 | 6/2019 | Walters et al. |
| 2019/0264139 A1 | 8/2019 | Lant et al. |
| 2020/0172831 A1 * | 6/2020 | Dhawan ................ B01D 65/02 |

FOREIGN PATENT DOCUMENTS

| | | |
|---|---|---|
| EP | 3415571 A1 | 12/2018 |
| WO | 2006/025928 A3 | 3/2006 |
| WO | 2007/008199 A1 | 1/2007 |
| WO | 2008/036559 A2 | 3/2008 |
| WO | 2019/067173 A1 | 4/2019 |
| WO | 2020/113218 A2 | 6/2020 |

OTHER PUBLICATIONS

Database CA [Online], Chemical Abstracts Service, Columbus, Ohio, US. Sun, Yu et al., Process for preparation of temperature resistant salt resistant polyether sulfonate, Database Accession No. 2013:638115; & CN 103 058 895 A (Jiangsu Maysta Chemical Co., Ltd.) Apr. 24, 2013, 3 pages.

Database CA [Online], Chemical Abstracts Service, Columbus, Ohio, US. Wang, Dongfang et al., Study on the Interfacial tension of the water solution of a new anionic-non-ionic surfactant and crude oil, Database Accession No. 2009:578202; Xi'an Shiyou Daxue Xuebao, Ziran Kexueban (2008) 23(6), 70-73, 2 pages.

Sherif, E.M. et al., Inhibition of Copper Corrosion in 3.0% NaCl Solution by N-Phenyl-1,4-phenylenediamine, Journal of The Electrochemical Society, 152 (10) (2005), pp. B428-B433.

* cited by examiner

ANTIFOULING COMPOUNDS USED FOR MICROBIAL FOULING CONTROL

CROSS REFERENCE TO RELATED APPLICATIONS

This application claims priority to U.S. Provisional Patent Application Ser. No. 63/034,274 filed on Jun. 3, 2020, the disclosure of which is incorporated herein by reference in its entirety.

FIELD OF THE INVENTION

Disclosed herein are antifouling compositions and uses of antifouling compositions for controlling microbial fouling in a system in contact with an aqueous medium. The antifouling compositions comprising an antifouling compound of Formula 1

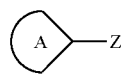
(1)

wherein A is an optionally substituted phenyl, naphthalene, indole, purine, pyridine, quinoline, isoquinoline, pyrimidine, pyrrole, furan, thiophene, imidazole, or thiazole; and Z has the following structure:

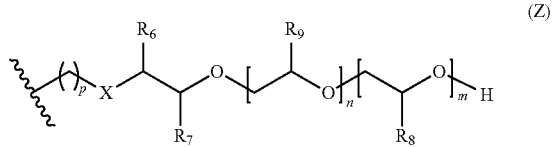
(Z)

wherein X is —O—, —N($R_{10}$)—, —OC(O)—, —C(O)O—, —N($R_{10}$)C(O)—, —C(O)N($R_{10}$)—, —OC(O)O—, —OC(O)N($R_{10}$)—, —N($R_{10}$)C(O)O—, or —N($R_{10}$)C(O) N($R_{10}$)—; p is an integer from 0 to 10; $R_6$ is hydrogen, alkyl, or aryl; $R_7$ is alkyl, aryl, or —(CH$_2$)z-O—$R_{11}$; $R_8$ and $R_9$ are independently hydrogen, alkyl or aryl; $R_{10}$ is hydrogen or alkyl; $R_{11}$ is hydrogen or alkyl; m is independently an integer from 2 to 20; n is independently an integer from 3 to 20; and z is an integer from 1 to 10, wherein at least one of $R_8$ and $R_9$ are other than hydrogen and wherein the antifouling composition reduces biofilm growth in a system comprising an aqueous medium.

BACKGROUND OF THE INVENTION

Fouling includes the deposition of an organic or an inorganic material on a surface. Many agents have been used to prevent fouling in industrial water systems and fouling can occur even when the water systems are treated with efficacious water treatment programs.

Without periodic cleaning, the industrial water systems will become heavily fouled and cause significant problems. For example, organic fouling will build up on the water contact surfaces and the presence of organic fouling provides an advantageous environment for microbial growth.

Evaporative cooling water systems are particularly prone to fouling. This fouling occurs by a variety of mechanisms including deposition of air-borne and water-borne and water-formed contaminants, water stagnation, process leaks, and other factors. If allowed to continue, the system can suffer from decreased operational efficiency, premature equipment failure, and increased health-related risks associated with microbial fouling.

Fouling can also occur due to microbial contamination. Sources of microbial contamination in industrial water systems are numerous and can include air-borne contamination, water make-up, process leaks and incompletely cleaned equipment. The microbes can grow on a wettable or semi-wettable surface of the system.

Additionally, substances secreted by microbes aid in the formation of biofilms as the microbe communities grow on the system's surfaces. The biofilms are complex systems that offer protection for microbe growth and can accelerate growth of scale, corrosion, and other fouling processes. The biofilms can also reduce the efficiency of the system in which the fouled surface is a component.

Thus, a need exists for effective and efficient methods to reduce fouling, particularly, microbial fouling of industrial water systems.

SUMMARY OF THE INVENTION

Disclosed herein are antifouling compositions and methods of controlling microbial fouling in a system comprising an aqueous medium.

For example, the antifouling compositions comprise an antifouling compound of Formula 1 having the following structure:

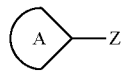
(1)

wherein A is an optionally substituted phenyl, naphthalene, indole, purine, pyridine, quinoline, isoquinoline, pyrimidine, pyrrole, furan, thiophene, imidazole, or thiazole; and Z has the following structure:

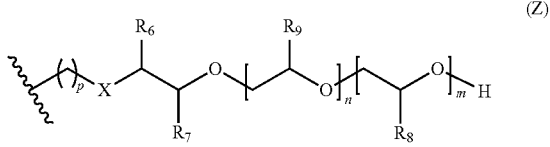
(Z)

wherein X is —O—, —N($R_{10}$)—, —OC(O)—, —C(O)O—, —N($R_{10}$)C(O)—, —C(O)N($R_{10}$)—, —OC(O)O—, —OC(O)N($R_{10}$)—, —N($R_{10}$)C(O)O—, or —N($R_{10}$)C(O) N($R_{10}$)—; p is an integer from 0 to 10; $R_6$ is hydrogen, alkyl, or aryl; $R_7$ is alkyl, aryl, or —(CH$_2$)z-O—$R_{11}$; $R_8$ and $R_9$ are independently hydrogen, alkyl or aryl; $R_{10}$ is hydrogen or alkyl; $R_{11}$ is hydrogen or alkyl; m is independently an integer from 2 to 20; n is independently an integer from 3 to 20; and z is an integer from 1 to 10, wherein at least one of $R_8$ and $R_9$ are other than hydrogen and wherein the antifouling composition reduces biofilm growth in a system comprising an aqueous medium.

The antifouling compounds of Formula 1 can have A be an optionally substituted phenyl, naphthyl, pyridyl, quinolyl, or isoquinolyl. Preferably, A is an optionally substituted phenyl or naphthyl.

The antifouling compositions described herein can have the antifouling compound of Formula 1 correspond to a structure of Formula 2:

$$\begin{array}{c} Z \\ R_5 \diagup\!\!\!\!\diagdown R_1 \\ R_4 \diagdown\!\!\!\!\diagup R_2 \\ R_3 \end{array} \quad (2)$$

wherein $R_1$, $R_2$, $R_3$, $R_4$, and $R_5$ are independently hydrogen, Z, alkyl, alkoxyl, or two adjacent R groups combine to form a fused ring.

The antifouling compounds of Formula 2 can have $R_1$, $R_2$, $R_3$, $R_4$, and $R_5$ independently be hydrogen or $C_1$ to $C_4$ alkyl; preferably, $R_1$, $R_2$, $R_3$, $R_4$, and $R_5$ are hydrogen.

The antifouling compounds of Formula 2 described herein can have $R_6$ be hydrogen.

As disclosed herein, the antifouling compounds of Formula 2 can have $R_8$ be methyl or benzyl.

Preferably, the antifouling compounds of Formula 2 can have $R_9$ be hydrogen.

The antifouling compounds of Formula 2 can further have $R_7$ be —$(CH_2)z$-O—$R_{11}$. Preferably, when $R_7$ is —$(CH_2)z$-O—$R_{11}$, z is 1 to 3. More preferably, when $R_7$ is —$(CH_2)z$-O—$R_{11}$, z is 1.

The antifouling compounds of Formula 2 described herein can have $R_{11}$ be $C_4$ to $C_{22}$ alkyl.

As disclosed herein, the antifouling compounds of Formula 2 can have X be —O— or —$N(R_{10})$—. Preferably, the antifouling compounds of Formula 2 can have X be —O—. Alternatively, the antifouling compounds of Formula 2 can have X be —$N(R_{10})$—.

The antifouling compound of Formula 2 can have $R_{10}$ be hydrogen.

The antifouling composition can have the antifouling compound of Formula 1 or 2 has a structure corresponding to wherein n is an integer from 10 to 20 and m is an integer from 2 to 12; preferably, wherein n is an integer of 16 or 18 and m is an integer from 4 to 8.

The antifouling composition further comprises a corrosion inhibitor.

The antifouling compositions described herein having the corrosion inhibitor be an imidazoline compound, a pyridinium compound, or a combination thereof.

As disclosed herein, the antifouling compositions can further comprise an additional antifouling agent, wherein the additional antifouling agent comprises a quaternary compound.

The antifouling compositions described herein can further comprise a biocide.

As disclosed herein, the antifouling compositions comprising a biocide can have the biocide be chlorine, hypochlorite, chlorine dioxide, bromine, ozone, hydrogen peroxide, peracetic acid, peroxycarboxylic acid, peroxycarboxylic acid composition, peroxysulfate, glutaraldehyde, dibromonitrilopropionamide, isothiazolone, terbutylazine, polymeric biguanide, methylene bisthiocyanate, tetrakis hydroxymethyl phosphonium sulfate, or a combination thereof.

The antifouling compositions also can further comprise a preservative or an acid.

As disclosed herein, the antifouling compositions comprising an acid, can have the acid be hydrochloric acid, hydrofluoric acid, citric acid, formic acid, acetic acid, or a mixture thereof.

The antifouling compositions can further comprise a hydrogen sulfide scavenger.

The antifouling compositions comprising a hydrogen sulfide scavenger can have the hydrogen sulfide scavenger be an oxidant, an inorganic peroxide, sodium peroxide, chlorine dioxide; a $C_1$-$C_{10}$ aldehyde, formaldehyde, glyoxal, glutaraldehyde, acrolein, methacrolein, a triazine, monoethanolamine triazine, monomethylamine triazine, or a mixture thereof.

As disclosed herein, the antifouling compositions can further comprise an asphaltene inhibitor, a paraffin inhibitor, a scale inhibitor, a gas hydrate inhibitor, a pH modifier, an emulsion breaker, a reverse emulsion breaker, a coagulant/flocculant agent, an emulsifier, a water clarifier, a dispersant, an antioxidant, a polymer degradation prevention agent, a permeability modifier, a foaming agent, an antifoaming agent, an emulsifying agent, a carbon dioxide scavenger agent, an oxygen scavenger agent, a gelling agent, a lubricant, a friction reducing agent, a salt, or a combination thereof.

The antifouling compositions can have the antifouling compound of Formula 1 or 2 be soluble or dispersible in water or the antifouling composition.

The antifouling compositions can comprise a carrier, wherein the carrier is water, an organic solvent, or a mixture thereof.

The antifouling compositions having a carrier of an organic solvent can have the organic solvent be an alcohol, a hydrocarbon, a ketone, an ether, an alkylene glycol, a glycol ether, an amide, a nitrile, a sulfoxide, an ester, or a combination thereof.

As disclosed herein, the antifouling compositions can comprise an organic solvent, wherein the organic solvent is (i) an alcohol, an alkylene glycol, an alkyleneglycol alkyl ether, or a combination thereof, (ii) methanol, ethanol, propanol, isopropanol, butanol, isobutanol, monoethyleneglycol, ethyleneglycol monobutyl ether, or a combination thereof, or (iii) methanol, ethanol, propanol, isopropanol, butanol, 2-ethylhexanol, hexanol, octanol, decanol, 2-butoxyethanol, methylene glycol, ethylene glycol, 1,2-propylene glycol, 1,3-propylene glycol, diethyleneglycol monomethyl ether, diethyl glycol monoethyl ether, ethylene glycol monobutyl ether, ethylene glycol dibutyl ether, pentane, hexane, cyclohexane, methylcyclohexane, heptane, decane, dodecane, diesel, toluene, xylene, heavy aromatic naphtha, cyclohexanone, diisobutylketone, diethyl ether, propylene carbonate, N-methylpyrrolidinone, N,N-dimethylformamide, a mixture thereof with water, or a combination thereof.

The antifouling compositions can be a liquid, gel, or a mixture comprising liquid/gel and solid.

The antifouling compositions disclosed herein can have a pH of from about 2 to about 11.

The antifouling compositions can comprise from about 0.1 wt. % to about 5 wt. % of the antifouling compound of Formula 1 or 2.

Also disclosed herein are methods of controlling microbial fouling in a system comprising an aqueous medium, the method comprising contacting the system with an antifouling composition as described herein, wherein the antifouling composition reduces bacterial growth or biofilm growth in the system comprising an aqueous medium.

For the methods of controlling microbial fouling, the aqueous medium can comprise fresh water, recycled water, salt water, surface water, produced water, or a mixture thereof.

Also, for the methods of controlling microbial fouling, the water system can be a cooling water system, a boiler water system, a petroleum well, a downhole formation, a geothermal well, a mineral washing system, a flotation and benefaction system, a papermaking system, a gas scrubber, an air washer, a continuous casting process in the metallurgical industry, an air conditioning and refrigeration system, a water reclamation system, a water purification system, a membrane filtration system, a food processing system, a clarifier system, a municipal sewage treatment system, a municipal water treatment system, or a potable water system.

The methods of controlling microbial fouling described herein can have the antifouling compound have a concentration of from about 0.001 ppm to about 1000 ppm in the aqueous medium.

Other objects and features will be in part apparent and in part pointed out hereinafter.

DESCRIPTION OF THE PREFERRED EMBODIMENTS

Disclosed herein is a novel antifouling compound, and compositions and methods for its use to control microbial fouling. These antifouling compounds and compositions are non-ionic oxyalkylated surface active compounds alkoxylated with varying amounts of ethylene oxide and propylene oxide. The disclosed antifouling compounds and compositions are highly efficacious for reducing or inhibiting biofilm growth, particularly when using mixed bacterial populations found in cooling waters and mixed *Pseudomonas* species as test microorganisms. The effective concentration of the antifouling compositions can be from about 16 ppm to about 125 ppm. Some of the antifouing compounds and compositions were more effective than a non-oxidizing quaternary ammonium biocide product Nalco 90005 (a dioctyl dimethyl ammonium chloride).

An important advantage of these antifouling compounds and compositions includes their compatibility with other cooling water treatment agents because of their non-ionic nature. The antifouling compounds and compositions are also useful for surface biofouling control. The advantageous properties of the disclosed antifouling compounds and compositions allow for their use in multifunctional product formulations that treat multiple issues of the industrial waters. Further, the antifouling compounds and compositions can provide for reduced biocide usage and higher biocide efficiency.

Disclosed herein are antifouling compositions and methods of controlling microbial fouling in a system comprising an aqueous medium. For example, the antifouling compositions comprise an antifouling compound of Formula 1 having the following structure:

(1)

wherein A is an optionally substituted phenyl, naphthalene, indole, purine, pyridine, quinoline, isoquinoline, pyrimidine, pyrrole, furan, thiophene, imidazole, or thiazole; and Z has the following structure:

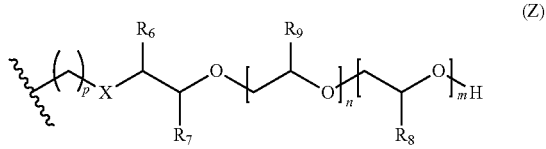
(Z)

wherein X is —O—, —N($R_{10}$)—, —OC(O)—, —C(O)O—, —N($R_{10}$)C(O)—, —C(O)N($R_{10}$)—, —OC(O)O—, —OC(O)N($R_{10}$)—, —N($R_{10}$)C(O)O—, or —N($R_{10}$)C(O) N($R_{10}$)—; p is an integer from 0 to 10; $R_6$ is hydrogen, alkyl, or aryl; $R_7$ is alkyl, aryl, or —($CH_2$) z-O—$R_{11}$; $R_8$ and $R_9$ are independently hydrogen, alkyl or aryl; $R_{10}$ is hydrogen or alkyl; $R_{11}$ is hydrogen or alkyl; m is independently an integer from 2 to 20; n is independently an integer from 3 to 20; and z is an integer from 1 to 10, wherein at least one of $R_8$ and $R_9$ are other than hydrogen and wherein the antifouling composition reduces biofilm growth in a system comprising an aqueous medium.

The antifouling compounds of Formula 1 can have A be an optionally substituted phenyl, naphthyl, pyridyl, quinolyl, or isoquinolyl. Preferably, A is an optionally substituted phenyl or naphthyl.

The antifouling compositions described herein can have the antifouling compound of Formula 1 correspond to a structure of Formula 2:

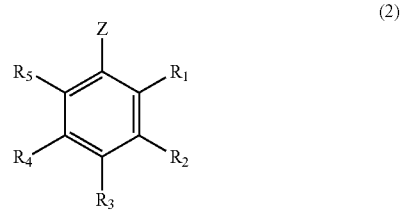
(2)

wherein $R_1$, $R_2$, $R_3$, $R_4$, and $R_5$ are independently hydrogen, Z, alkyl, alkoxyl, or two adjacent R groups combine to form a fused ring.

The antifouling compounds of Formula 2 can have $R_1$, $R_2$, $R_3$, $R_4$, and $R_5$ independently be hydrogen or $C_1$ to $C_4$ alkyl; preferably, $R_1$, $R_2$, $R_3$, $R_4$, and $R_5$ are hydrogen.

The antifouling compounds of Formula 2 described herein can have $R_6$ be hydrogen.

As disclosed herein, the antifouling compounds of Formula 2 can have $R_8$ be methyl or benzyl.

Preferably, the antifouling compounds of Formula 2 can have $R_9$ be hydrogen.

The antifouling compounds of Formula 2 can further have $R_7$ be —$(CH_2)z$-O—$R_{11}$. Preferably, when $R_7$ is —$(CH_2)z$-O—$R_{11}$, z is 1 to 3. More preferably, when $R_7$ is —$(CH_2)z$-O—$R_{11}$, z is 1.

The antifouling compounds of Formula 2 described herein can have $R_{11}$ be $C_4$ to $C_{22}$ alkyl.

As disclosed herein, the antifouling compounds of Formula 2 can have X be —O— or —$N(R_{10})$—. Preferably, the antifouling compounds of Formula 2 can have X be —O—. Alternatively, the antifouling compounds of Formula 2 can have X be —$N(R_{10})$—.

The antifouling compound of Formula 2 can have $R_{10}$ be hydrogen.

The antifouling composition can have the antifouling compound of Formula 1 or 2 has a structure corresponding to

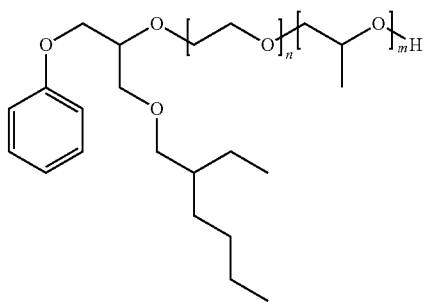

wherein n is an integer from 10 to 20 and m is an integer from 2 to 12; preferably, wherein n is an integer of 16 or 18 and m is an integer from 4 to 8.

The antifouling composition further comprises a corrosion inhibitor.

The antifouling compositions described herein having the corrosion inhibitor be an imidazoline compound, a pyridinium compound, or a combination thereof.

As disclosed herein, the antifouling compositions can further comprise an additional antifouling agent, wherein the additional antifouling agent comprises a quaternary compound.

The antifouling compositions described herein can further comprise a biocide.

As disclosed herein, the antifouling compositions comprising a biocide can have the biocide be chlorine, hypochlorite, chlorine dioxide, bromine, ozone, hydrogen peroxide, peracetic acid, peroxycarboxylic acid, peroxycarboxylic acid composition, peroxysulfate, glutaraldehyde, dibromonitrilopropionamide, isothiazolone, terbutylazine, polymeric biguanide, methylene bisthiocyanate, tetrakis hydroxymethyl phosphonium sulfate, or a combination thereof.

The antifouling compositions also can further comprise a preservative or an acid.

As disclosed herein, the antifouling compositions comprising an acid, can have the acid be hydrochloric acid, hydrofluoric acid, citric acid, formic acid, acetic acid, or a mixture thereof.

The antifouling compositions can further comprise a hydrogen sulfide scavenger.

The antifouling compositions comprising a hydrogen sulfide scavenger can have the hydrogen sulfide scavenger be an oxidant, an inorganic peroxide, sodium peroxide, chlorine dioxide; a $C_1$-$C_{10}$ aldehyde, formaldehyde, glyoxal, glutaraldehyde, acrolein, methacrolein, a triazine, monoethanolamine triazine, monomethylamine triazine, or a mixture thereof.

As disclosed herein, the antifouling compositions can further comprise an asphaltene inhibitor, a paraffin inhibitor, a scale inhibitor, a gas hydrate inhibitor, a pH modifier, an emulsion breaker, a reverse emulsion breaker, a coagulant/flocculant agent, an emulsifier, a water clarifier, a dispersant, an antioxidant, a polymer degradation prevention agent, a permeability modifier, a foaming agent, an antifoaming agent, an emulsifying agent, a carbon dioxide scavenger agent, an oxygen scavenger agent, a gelling agent, a lubricant, a friction reducing agent, a salt, or a combination thereof.

The antifouling compositions can have the antifouling compound of Formula 1 or 2 be soluble or dispersible in water or the antifouling composition.

The antifouling compositions can comprise a carrier, wherein the carrier is water, an organic solvent, or a mixture thereof.

The antifouling compositions having a carrier of an organic solvent can have the organic solvent be an alcohol, a hydrocarbon, a ketone, an ether, an alkylene glycol, a glycol ether, an amide, a nitrile, a sulfoxide, an ester, or a combination thereof.

As disclosed herein, the antifouling compositions can comprise an organic solvent, wherein the organic solvent is (i) an alcohol, an alkylene glycol, an alkyleneglycol alkyl ether, or a combination thereof, (ii) methanol, ethanol, propanol, isopropanol, butanol, isobutanol, monoethyleneglycol, ethyleneglycol monobutyl ether, or a combination thereof, or (iii) methanol, ethanol, propanol, isopropanol, butanol, 2-ethylhexanol, hexanol, octanol, decanol, 2-butoxyethanol, methylene glycol, ethylene glycol, 1,2-propylene glycol, 1,3-propylene glycol, diethyleneglycol monomethyl ether, diethylene glycol monoethyl ether, ethylene glycol monobutyl ether, ethylene glycol dibutyl ether, pentane, hexane, cyclohexane, methylcyclohexane, heptane, decane, dodecane, diesel, toluene, xylene, heavy aromatic naphtha, cyclohexanone, diisobutylketone, diethyl ether, propylene carbonate, N-methylpyrrolidinone, N,N-dimethylformamide, a mixture thereof with water, or a combination thereof.

The antifouling compositions can be a liquid, gel, or a mixture comprising liquid/gel and solid.

The antifouling compositions disclosed herein can have a pH of from about 2 to about 11.

The antifouling compositions can comprise from about 0.1 wt. % to about 5 wt. %, from about 0.25 wt. % to about 5 wt. %, from about 0.5 wt. % to about 5 wt. %, from about 0.75 wt. % to about 5 wt. %, from about 1 wt. % to about 5 wt. %, from about 0.1 wt. % to about 4 wt. %, from about 0.25 wt. % to about 4 wt. %, from about 0.5 wt. % to about 4 wt. %, from about 0.75 wt. % to about 4 wt. %, from about 1 wt. % to about 4 wt. %, from about 0.1 wt. % to about 3 wt. %, from about 0.25 wt. % to about 3 wt. %, from about 0.5 wt. % to about 3 wt. %, from about 0.75 wt. % to about 3 wt. %, from about 1 wt. % to about 3 wt. % of the antifouling compound of Formula 1 or 2.

Also disclosed herein are methods of controlling microbial fouling in a system comprising an aqueous medium, the method comprising contacting the system with an antifouling composition as described herein, wherein the antifouling composition reduces bacterial growth or biofilm growth in the system comprising an aqueous medium.

For the methods of controlling microbial fouling, the aqueous medium can comprise fresh water, recycled water, salt water, surface water, produced water, or a mixture thereof.

Also, for the methods of controlling microbial fouling, the water system can be a cooling water system, a boiler water system, a petroleum well, a downhole formation, a geothermal well, a mineral washing system, a flotation and benefaction system, a papermaking system, a gas scrubber, an air washer, a continuous casting process in the metallurgical industry, an air conditioning and refrigeration system, a water reclamation system, a water purification system, a membrane filtration system, a food processing system, a clarifier system, a municipal sewage treatment system, a municipal water treatment system, or a potable water system.

The methods of controlling microbial fouling described herein can have the antifouling compound have a concentration of from about 0.001 ppm to about 1000 ppm, from about 0.01 ppm to about 1000 ppm, from about 0.1 ppm to about 1000 ppm, from about 1 ppm to about 1000 ppm, from about 10 ppm to about 1000 ppm, from about 15 ppm to about 1000 ppm, from about 0.001 ppm to about 750 ppm, from about 0.01 ppm to about 750 ppm, from about 0.1 ppm to about 750 ppm, from about 1 ppm to about 750 ppm, from about 10 ppm to about 750 ppm, from about 15 ppm to about 750 ppm, from about 0.001 ppm to about 500 ppm, from about 0.01 ppm to about 500 ppm, from about 0.1 ppm to about 500 ppm, from about 1 ppm to about 500 ppm, from about 10 ppm to about 500 ppm, from about 15 ppm to about 500 ppm, from about 0.001 ppm to about 250 ppm, from about 0.01 ppm to about 250 ppm, from about 0.1 ppm to about 250 ppm, from about 1 ppm to about 250 ppm, from about 10 ppm to about 250 ppm, from about 15 ppm to about 250 ppm based on the total weight of the aqueous medium.

The overall synthesis of the antifouling compounds described herein is achieved in two steps (Scheme 1). Acceptor molecule (C) is first prepared by ring opening reaction of an alkyl-epoxide (B) with an aromatic amine or alcohol compound (A). The second step involves oxyalkylation of the acceptor molecule (C) with one or more alkylene oxides (D & E) to afford a series of surfactants (F).

Scheme 1

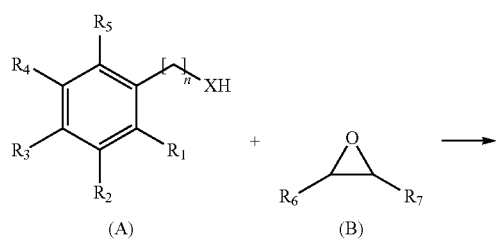

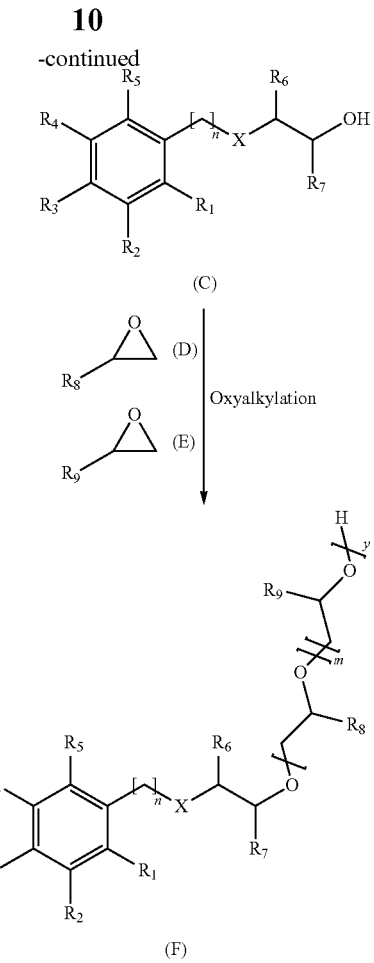

wherein X is —O—, —N($R_{10}$)—, —OC(O)—, —C(O)O—, —N($R_{10}$)C(O)—, —C(O)N($R_{10}$)—, —OC(O)O—, —OC(O)N($R_{10}$)—, —N($R_{10}$)C(O)O—, or —N($R_{10}$)C(O) N($R_{10}$)—; n is an integer from 0 to 10; $R_6$ and $R_9$ are independently hydrogen, alkyl, or aryl; $R_7$ is alkyl, aryl, or —(CH$_2$)z-O—$R_{11}$, $R_8$ is independently hydrogen, alkyl, or aryl; $R_{10}$ is hydrogen, alkyl, or Z; $R_{11}$ is hydrogen or alkyl; m is independently an integer from 3 to 20; y is independently an integer from 3 to 20; and z is an integer from 1 to 10; and $R_1$, $R_2$, $R_3$, $R_4$, and $R_5$ are independently hydrogen, Z, alkyl, alkoxyl, or two adjacent R groups combine to form a fused ring. Preferably, $R_8$ is hydrogen and $R_9$ is methyl.

The antifouling compositions can comprise an antifouling compound of Formula 1 or 2 and a component selected from the group consisting of an organic solvent, a corrosion inhibitor, an asphaltene inhibitor, a paraffin inhibitor, a scale inhibitor, an emulsifier, a water clarifier, a dispersant, an emulsion breaker, a gas hydrate inhibitor, a biocide, a pH modifier, a surfactant, and a combination thereof.

The composition can comprise from about 20 to about 90 wt. % of the antifouling compound and from about 10 to about 80 wt. % of the component, preferably from about 50 to about 90 wt. % of one or more antifouling compound and from about 10 to about 50 wt. % of the component, and more preferably from about 65 to about 85 wt. % of one or more antifouling compound and from about 15 to about 35 wt. % of the component.

The component of the composition can comprise an organic solvent. The composition can comprise from about 1 to 80 wt. %, from about 5 to 50 wt. %, or from about 10 to 35 wt. % of the one or more organic solvents, based on total weight of the composition. The organic solvent can comprise an alcohol, a hydrocarbon, a ketone, an ether, an alkylene glycol, a glycol ether, an amide, a nitrile, a sulfoxide, an ester, or a combination thereof. Examples of suitable organic solvents include, but are not limited to, methanol, ethanol, propanol, isopropanol, butanol, 2-ethylhexanol, hexanol, octanol, decanol, 2-butoxyethanol, methylene glycol, ethylene glycol, 1,2-propylene glycol, 1,3-propylene glycol, diethyleneglycol monomethyl ether, diethylene glycol monoethyl ether, ethylene glycol monobutyl ether, ethylene glycol dibutyl ether, pentane, hexane, cyclohexane, methylcyclohexane, heptane, decane, dodecane, diesel, toluene, xylene, heavy aromatic naphtha, cyclohexanone, diisobutylketone, diethyl ether, propylene carbonate, N-methylpyrrolidinone, N,N-dimethylformamide, or a combination thereof.

The component of the composition can comprise a corrosion inhibitor. The composition can comprise from about 0.1 to 20 wt. %, 0.1 to 10 wt. %, or 0.1 to 5 wt. % of the corrosion inhibitors, based on total weight of the composition. A composition can comprise from 0.1 to 10 percent by weight of the corrosion inhibitors, based on total weight of the composition. The composition can comprise 1.0 wt %, 1.5 wt %, 2.0 wt %, 2.5 wt %, 3.0 wt %, 3.5 wt %, 4.0 wt %, 4.5 wt %, 5.0 wt %, 5.5 wt %, 6.0 wt %, 6.5 wt %, 7.0 wt %, 7.5 wt %, 8.0 wt %, 8.5 wt %, 9.0 wt %, 9.5 wt %, 10.0 wt %, 10.5 wt %, 11.0 wt %, 11.5 wt %, 12.0 wt %, 12.5 wt %, 13.0 wt %, 13.5 wt %, 14.0 wt %, 14.5 wt %, or 15.0 wt % by weight of the corrosion inhibitors, based on total weight of the composition. Each system can have its own requirements, and the weight percent of one or more additional corrosion inhibitors in the composition can vary with the system in which it is used.

The corrosion inhibitor can comprise an imidazoline compound, a quaternary ammonium compound, a pyridinium compound, or a combination thereof.

The corrosion inhibitor component can comprise an imidazoline. The imidazoline can be, for example, imidazoline derived from a diamine, such as ethylene diamine (EDA), diethylene triamine (DETA), triethylene tetraamine (TETA) etc. and a long chain fatty acid such as tall oil fatty acid (TOFA). The imidazoline can be an imidazoline of Formula (I) or an imidazoline derivative. Representative imidazoline derivatives include an imidazolinium compound of Formula (II) or a bis-quaternized compound of Formula (III).

The corrosion inhibitor component can include an imidazoline of Formula (I):

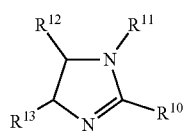

(I)

wherein $R^{10}$ is a $C_1$-$C_{20}$ alkyl or a $C_1$-$C_{20}$ alkoxyalkyl group; $R^{11}$ is hydrogen, $C_1$-$C_6$ alkyl, $C_1$-$C_6$ hydroxyalkyl, or $C_1$-$C_6$ arylalkyl; and $R^{12}$ and $R^{13}$ are independently hydrogen or a $C_1$-$C_6$ alkyl group. Preferably, the imidazoline includes an $R^{10}$, which is the alkyl mixture typical in tall oil fatty acid (TOFA), and $R^{11}$, $R^{12}$ and $R^{13}$ are each hydrogen.

The corrosion inhibitor component can include an imidazolinium compound of Formula (II):

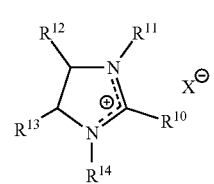

(II)

wherein $R^{10}$ is a $C_1$-$C_{20}$ alkyl or a $C_1$-$C_{20}$ alkoxyalkyl group; $R^{11}$ and $R^{14}$ are independently hydrogen, $C_1$-$C_6$ alkyl, $C_1$-$C_6$ hydroxyalkyl, or $C_1$-$C_6$ arylalkyl; $R^{12}$ and $R^{13}$ are independently hydrogen or a $C_1$-$C_6$ alkyl group; and $X^-$ is a halide (such as chloride, bromide, or iodide), carbonate, sulfonate, phosphate, or the anion of an organic carboxylic acid (such as acetate). Preferably, the imidazolinium compound includes 1-benzyl-1-(2-hydroxyethyl)-2-tall-oil-2-imidazolinium chloride.

The corrosion inhibitor can comprise a bis-quaternized compound having the formula (III):

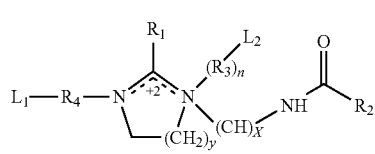

(III)

wherein $R_1$ and $R_2$ are each independently unsubstituted branched, chain or ring alkyl or alkenyl having from 1 to about 29 carbon atoms; partially or fully oxygenized, sulfurized, and/or phosphorylized branched, chain, or ring alkyl or alkenyl having from 1 to about 29 carbon atoms; or a combination thereof; $R_3$ and $R_4$ are each independently unsubstituted branched, chain or ring alkylene or alkenylene having from 1 to about 29 carbon atoms; partially or fully oxygenized, sulfurized, and/or phosphorylized branched, chain, or ring alkylene or alkenylene having from 1 to about 29 carbon atoms; or a combination thereof; $L_1$ and $L_2$ are each independently absent, H, —COOH, —SO$_3$H, —PO$_3$H$_2$, —COOR$_5$, —CONH$_2$, —CONHR$_5$, or —CON(R$_5$)$_2$; $R_5$ is each independently a branched or unbranched alkyl, aryl, alkylaryl, alkylheteroaryl, cycloalkyl, or heteroaryl group having from 1 to about 10 carbon atoms; n is 0 or 1, and when n is 0, $L_2$ is absent or H; x is from 1 to about 10; and y is from 1 to about 5. Preferably, $R_1$ and $R_2$ are each independently $C_6$-$C_{22}$ alkyl, $C_8$-$C_{20}$ alkyl, $C_{12}$-$C_{18}$ alkyl, $C_{16}$-$C_{18}$ alkyl, or a combination thereof; $R_3$ and $R_4$ are $C_1$-$C_{10}$ alkylene, $C_2$-$C_8$ alkylene, $C_2$-$C_6$ alkylene, or $C_2$-$C_3$ alkylene; n is 0 or 1; x is 2; y is 1; $R_3$ and $R_4$ are —C$_2$H$_2$—; $L_1$ is —COOH, —SO$_3$H, or —PO$_3$H$_2$; and $L_2$ is absent, H, —COOH, —SO$_3$H, or —PO$_3$H$_2$. For example, $R_1$ and $R_2$ can be derived from a mixture of tall oil fatty acids and are predominantly a mixture of $C_{17}H_{33}$ and $C_{17}H_{31}$ or can be $C_{16}$-$C_{18}$ alkyl; $R_3$ and $R_4$ can be $C_2$-$C_3$ alkylene such as —C$_2$H$_2$—; n is 1 and $L_2$ is —COOH or n is 0 and $L_2$ is absent or H; x is 2; y is 1; $R_3$ and $R_4$ are —C$_2$H$_2$—; and $L_1$ is —COOH.

It should be appreciated that the number of carbon atoms specified for each group of formula (III) refers to the main chain of carbon atoms and does not include carbon atoms that may be contributed by substituents.

The corrosion inhibitor can comprise a bis-quaternized imidazoline compound having the formula (III) wherein $R_1$ and $R_2$ are each independently $C_6$-$C_{22}$ alkyl, $C_8$-$C_{20}$ alkyl, $C_{12}$-$C_{18}$ alkyl, or $C_{16}$-$C_{18}$ alkyl or a combination thereof; $R_4$ is $C_1$-$C_{10}$ alkylene, $C_2$-$C_8$ alkylene, $C_2$-$C_6$ alkylene, or $C_2$-$C_3$ alkylene; x is 2; y is 1; n is 0; $L_1$ is —COOH, —SO$_3$H, or —PO$_3$H$_2$; and $L_2$ is absent or H. Preferably, a bis-quaternized compound has the formula (III) wherein $R_1$ and $R_2$ are each independently $C_{16}$-$C_{18}$ alkyl; $R_4$ is —C$_2$H$_2$—; x is 2; y is 1; n is 0; $L_1$ is —COOH, —SO$_3$H, or —PO$_3$H$_2$ and $L_2$ is absent or H.

The corrosion inhibitor can be a quaternary ammonium compound of Formula (IV):

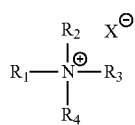

(IV)

wherein $R_1$, $R_2$, and $R_3$ are independently $C_1$ to $C_{20}$ alkyl, $R_4$ is methyl or benzyl, and $X^-$ is a halide or methosulfate.

Suitable alkyl, hydroxyalkyl, alkylaryl, arylalkyl or aryl amine quaternary salts include those alkylaryl, arylalkyl and aryl amine quaternary salts of the formula [N$^+$R$^{5a}$R$^{6a}$R$^{7a}$R$^{8a}$][X$^-$] wherein R$^{5a}$, R$^{6a}$, R$^{7a}$, and R$^{8a}$ contain one to 18 carbon atoms, and X is Cl, Br or I. For the quaternary salts, R$^{5a}$, R$^{6a}$, R$^{7a}$, and R$^{8a}$ can each be independently selected from the group consisting of alkyl (e.g., $C_1$-$C_{18}$ alkyl), hydroxyalkyl (e.g., $C_1$-$C_{18}$ hydroxyalkyl), and arylalkyl (e.g., benzyl). The mono or polycyclic aromatic amine salt with an alkyl or alkylaryl halide include salts of the formula [N$^+$R$^{5a}$R$^{6a}$R$^{7a}$R$^{8a}$][X$^-$] wherein R$^{5a}$, R$^{6a}$, R$^{7a}$, and R$^{8a}$ contain one to 18 carbon atoms and at least one aryl group, and X is Cl, Br or I.

Suitable quaternary ammonium salts include, but are not limited to, a tetramethyl ammonium salt, a tetraethyl ammonium salt, a tetrapropyl ammonium salt, a tetrabutyl ammonium salt, a tetrahexyl ammonium salt, a tetraoctyl ammonium salt, a benzyltrimethyl ammonium salt, a benzyltriethyl ammonium salt, a phenyltrimethyl ammonium salt, a phenyltriethyl ammonium salt, a cetyl benzyldimethyl ammonium salt, a hexadecyl trimethyl ammonium salt, a dimethyl alkyl benzyl quaternary ammonium salt, a monomethyl dialkyl benzyl quaternary ammonium salt, or a trialkyl benzyl quaternary ammonium salt, wherein the alkyl group has about 6 to about 24 carbon atoms, about 10 and about 18 carbon atoms, or about 12 to about 16 carbon atoms. The quaternary ammonium salt can be a benzyl trialkyl quaternary ammonium salt, a benzyl triethanolamine quaternary ammonium salt, or a benzyl dimethylaminoethanolamine quaternary ammonium salt.

The corrosion inhibitor component can comprise a pyridinium salt such as those represented by Formula (V):

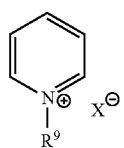

(V)

wherein $R^9$ is an alkyl group, an aryl group, or an arylalkyl group, wherein said alkyl groups have from 1 to about 18 carbon atoms and $X^-$ is a halide such as chloride, bromide, or iodide. Among these compounds are alkyl pyridinium salts and alkyl pyridinium benzyl quats. Exemplary compounds include methyl pyridinium chloride, ethyl pyridinium chloride, propyl pyridinium chloride, butyl pyridinium chloride, octyl pyridinium chloride, decyl pyridinium chloride, lauryl pyridinium chloride, cetyl pyridinium chloride, benzyl pyridinium chloride and an alkyl benzyl pyridinium chloride, preferably wherein the alkyl is a $C_1$-$C_6$ hydrocarbyl group. Preferably, the pyridinium compound includes benzyl pyridinium chloride.

The corrosion inhibitor components can include additional corrosion inhibitors such as phosphate esters, monomeric or oligomeric fatty acids, or alkoxylated amines.

The corrosion inhibitor component can comprise a phosphate ester. Suitable mono-, di- and tri-alkyl as well as alkylaryl phosphate esters and phosphate esters of mono, di, and triethanolamine typically contain between from 1 to about 18 carbon atoms. Preferred mono-, di- and trialkyl phosphate esters, alkylaryl or arylalkyl phosphate esters are those prepared by reacting a $C_3$-$C_{15}$ aliphatic alcohol with phosphorous pentoxide. The phosphate intermediate interchanges its ester groups with triethylphosphate producing a more broad distribution of alkyl phosphate esters.

Alternatively, the phosphate ester can be made by admixing with an alkyl diester, a mixture of low molecular weight alkyl alcohols or diols. The low molecular weight alkyl alcohols or diols preferably include $C_6$ to $C_{10}$ alcohols or diols. Further, phosphate esters of polyols and their salts containing one or more 2-hydroxyethyl groups, and hydroxylamine phosphate esters obtained by reacting polyphosphoric acid or phosphorus pentoxide with hydroxylamines such as diethanolamine or triethanolamine are preferred.

The corrosion inhibitor component can include a monomeric or oligomeric fatty acid. Preferred monomeric or oligomeric fatty acids are $C_{14}$-$C_{22}$ saturated and unsaturated fatty acids as well as dimer, trimer and oligomer products obtained by polymerizing one or more of such fatty acids.

The corrosion inhibitor component can comprise an alkoxylated amine. The alkoxylated amine can be an ethoxylated alkyl amine. The alkoxylated amine can be ethoxylated tallow amine.

The component of the composition can comprise an organic sulfur compound, such as a mercaptoalkyl alcohol, mercaptoacetic acid, thioglycolic acid, 3,3'-dithiodipropionic acid, sodium thiosulfate, thiourea, L-cysteine, tert-butyl mercaptan, sodium thiosulfate, ammonium thiosulfate, sodium thiocyanate, ammonium thiocyanate, sodium metabisulfite, or a combination thereof. Preferably, the mercaptoalkyl alcohol comprises 2-mercaptoethanol. The organic sulfur compound can constitute 0.5 to 15 wt. % of the composition, based on total weight of the composition, preferably about 1 to about 10 wt. % and more preferably about 1 to about 5 wt. %. The organic sulfur compound can constitute 1, 2, 3, 4, 5, 6, 7, 8, 9, 10, 11, 12, 13, 14 or 15 wt. % of the composition.

The composition can be substantially free of or free of any organic sulfur compound other than the compound of formula (1). A composition is substantially free of any organic sulfur compound if it contains an amount of organic sulfur compound below the amount that will produce hydrogen sulfide gas upon storage at a temperature of 25° C. and ambient pressure.

The component of the composition can further include a demulsifier. Preferably, the demulsifier comprises an oxyalkylate polymer, such as a polyalkylene glycol. The demulsifier can constitute from about 0.1 to 10 wt. %, from about 0.5 to 5 wt. %, or from about 0.5 to 4 wt. % of the composition, based on total weight of the composition. The demulsifier can constitute 0.5, 1, 1.5, 2, 2.5, 3, 3.5, 4, 4.5 or 5 wt. % of the composition.

The component of the composition can include an asphaltene inhibitor. The composition can comprise from about 0.1 to 10 wt. %, from about 0.1 to 5 wt. %, or from about 0.5 to 4 wt. % of an asphaltene inhibitor, based on total weight of the composition. Suitable asphaltene inhibitors include, but are not limited to, aliphatic sulfonic acids; alkyl aryl sulfonic acids; aryl sulfonates; lignosulfonates; alkylphenol/aldehyde resins and similar sulfonated resins; polyolefin esters; polyolefin imides; polyolefin esters with alkyl, alkylenephenyl or alkylenepyridyl functional groups; polyolefin amides; polyolefin amides with alkyl, alkylenephenyl or alkylenepyridyl functional groups; polyolefin imides with alkyl, alkylenephenyl or alkylenepyridyl functional groups; alkenyl/vinyl pyrrolidone copolymers; graft polymers of polyolefins with maleic anhydride or vinyl imidazole; hyperbranched polyester amides; polyalkoxylated asphaltenes, amphoteric fatty acids, salts of alkyl succinates, sorbitan monooleate, and polyisobutylene succinic anhydride.

The component of the composition can include an additional paraffin inhibitor. The composition can comprise from about 0.1 to 10 wt. %, from about 0.1 to 5 wt. %, or from about 0.5 to 4 wt. % of an additional paraffin inhibitor, based on total weight of the composition. Suitable additional paraffin inhibitors include, but are not limited to, paraffin crystal modifiers, and dispersant/crystal modifier combinations. Suitable paraffin crystal modifiers include, but are not limited to, alkyl acrylate copolymers, alkyl acrylate vinylpyridine copolymers, ethylene vinyl acetate copolymers, maleic anhydride ester copolymers, branched polyethylenes, naphthalene, anthracene, microcrystalline wax and/or asphaltenes. Suitable paraffin dispersants include, but are not limited to, dodecyl benzene sulfonate, oxyalkylated alkylphenols, and oxyalkylated alkylphenolic resins.

The component of the composition can include a scale inhibitor. The composition can comprise from about 0.1 to 20 wt. %, from about 0.5 to 10 wt. %, or from about 1 to 10 wt. % of a scale inhibitor, based on total weight of the composition. Suitable scale inhibitors include, but are not limited to, phosphates, phosphate esters, phosphoric acids, phosphonates, phosphonic acids, polyacrylamides, salts of acrylamidomethyl propane sulfonate/acrylic acid copolymer (AMPS/AA), phosphinated maleic copolymer (PHOS/MA), and salts of a polymaleic acid/acrylic acid/acrylamidomethyl propane sulfonate terpolymer (PMA/AA/AMPS).

The component of the composition can include an emulsifier. The composition can comprise from about 0.1 to 10 wt. %, from about 0.5 to 5 wt. %, or from about 0.5 to 4 wt. % of an emulsifier, based on total weight of the composition. Suitable emulsifiers include, but are not limited to, salts of carboxylic acids, products of acylation reactions between carboxylic acids or carboxylic anhydrides and amines, and alkyl, acyl and amide derivatives of saccharides (alkylsaccharide emulsifiers).

The component of the composition can include a water clarifier. The composition can comprise from about 0.1 to 10 wt. %, from about 0.5 to 5 wt. %, or from about 0.5 to 4 wt. % of a water clarifier, based on total weight of the composition. Suitable water clarifiers include, but are not limited to, inorganic metal salts such as alum, aluminum chloride, and aluminum chlorohydrate, or organic polymers such as acrylic acid based polymers, acrylamide based polymers, polymerized amines, alkanolamines, thiocarbamates, and cationic polymers such as diallyldimethylammonium chloride (DADMAC).

The component of the composition can include a dispersant. The composition can comprise from about 0.1 to 10 wt. %, from about 0.5 to 5 wt. %, or from about 0.5 to 4 wt. % of a dispersant, based on total weight of the composition. Suitable dispersants include, but are not limited to, aliphatic phosphonic acids with 2-50 carbons, such as hydroxyethyl diphosphonic acid, and aminoalkyl phosphonic acids, e.g. polyaminomethylene phosphonates with 2-10 N atoms e.g. each bearing at least one methylene phosphonic acid group; examples of the latter are ethylenediamine tetra(methylene phosphonate), diethylenetriamine penta(methylene phosphonate), and the triamine- and tetramine-polymethylene phosphonates with 2-4 methylene groups between each N atom, at least 2 of the numbers of methylene groups in each phosphonate being different. Other suitable dispersion agents include lignin, or derivatives of lignin such as lignosulfonate and naphthalene sulfonic acid and derivatives.

The component of the composition can include an emulsion breaker. The composition can comprise from about 0.1 to 10 wt. %, from about 0.5 to 5 wt. %, or from about 0.5 to 4 wt. % of an emulsion breaker, based on total weight of the composition. Suitable emulsion breakers include, but are not limited to, dodecylbenzylsulfonic acid (DDBSA), the sodium salt of xylenesulfonic acid (NAXSA), epoxylated and propoxylated compounds, anionic, cationic and non-ionic surfactants, and resins, such as phenolic and epoxide resins.

The component of the composition can include a hydrogen sulfide scavenger. The composition can comprise from about 1 to 50 wt. %, from about 1 to 40 wt. %, or from about 1 to 30 wt. % of a hydrogen sulfide scavenger, based on total weight of the composition. Suitable additional hydrogen sulfide scavengers include, but are not limited to, oxidants (e.g., inorganic peroxides such as sodium peroxide or chlorine dioxide); aldehydes (e.g., of 1-10 carbons such as formaldehyde, glyoxal, glutaraldehyde, acrolein, or methacrolein; triazines (e.g., monoethanolamine triazine, monomethylamine triazine, and triazines from multiple amines or mixtures thereof); condensation products of secondary or tertiary amines and aldehydes, and condensation products of alkyl alcohols and aldehydes.

The component of the composition can include a gas hydrate inhibitor. The composition can comprise from about 0.1 to 25 wt. %, from about 0.1 to 20 wt. %, or from about 0.3 to 20 wt. % of a gas hydrate inhibitor, based on total weight of the composition. Suitable gas hydrate inhibitors include, but are not limited to, thermodynamic hydrate inhibitors (THI), kinetic hydrate inhibitors (KHI), and anti-agglomerates (AA). Suitable thermodynamic hydrate inhibitors include, but are not limited to, sodium chloride, potassium chloride, calcium chloride, magnesium chloride, sodium bromide, formate brines (e.g. potassium formate), polyols (such as glucose, sucrose, fructose, maltose, lactose, gluconate, monoethylene glycol, diethylene glycol, triethylene glycol, mono-propylene glycol, dipropylene glycol, tripropylene glycols, tetrapropylene glycol, monobutylene glycol, dibutylene glycol, tributylene glycol, glycerol, diglycerol, triglycerol, and sugar alcohols (e.g. sorbitol, mannitol)), methanol, propanol, ethanol, glycol ethers (such as diethyleneglycol monomethylether, ethyleneglycol monobutylether), and alkyl or cyclic esters of alcohols (such as ethyl lactate, butyl lactate, methylethyl benzoate).

The component of the composition can include a kinetic hydrate inhibitor. The composition can comprise from about 5 to 30 wt. %, from about 5 to 25 wt. %, or from about 10 to 25 wt. % of a kinetic hydrate inhibitor, based on total weight of the composition. Suitable kinetic hydrate inhibitors and anti-agglomerates include, but are not limited to, polymers and copolymers, polysaccharides (such as hydroxyethylcellulose (HEC), carboxymethylcellulose (CMC), starch, starch derivatives, and xanthan), lactams (such as polyvinylcaprolactam, polyvinyl lactam), pyrrolidones (such as polyvinyl pyrrolidone of various molecular weights), surfactants (such as fatty acid salts, ethoxylated alcohols, propoxylated alcohols, sorbitan esters, ethoxylated sorbitan esters, polyglycerol esters of fatty acids, alkyl glucosides, alkyl polyglucosides, alkyl sulfates, alkyl sulfonates, alkyl ester sulfonates, alkyl aromatic sulfonates, alkyl betaine, alkyl amido betaines), hydrocarbon based dispersants (such as lignosulfonates, iminodisuccinates, polyaspartates), amino acids, and proteins.

The component of the composition can include a biocide. The composition can comprise from about 0.1 to 35 wt. %, from about 10 to 35 wt. %, or from about 15 to 35 wt. % of a biocide, based on total weight of the composition. Suitable biocides include, but are not limited to, oxidizing and non-oxidizing biocides. Suitable non-oxidizing biocides include, for example, aldehydes (e.g., formaldehyde, glutaraldehyde, and acrolein), amine-type compounds (e.g., quaternary amine compounds and cocodiamine), halogenated compounds (e.g., 2-bromo-2-nitropropane-3-diol (Bronopol) and 2-2-dibromo-3-nitrilopropionamide (DBNPA)), sulfur compounds (e.g., isothiazolone, carbamates, and metronidazole), and quaternary phosphonium salts (e.g., tetrakis(hydroxymethyl)-phosphonium sulfate (THPS)). Suitable oxidizing biocides include, for example, sodium hypochlorite, trichloroisocyanuric acids, dichloroisocyanuric acid, calcium hypochlorite, lithium hypochlorite, chlorinated hydantoins, stabilized sodium hypobromite, activated sodium bromide, brominated hydantoins, chlorine dioxide, ozone, peroxides, biguanine, formaldehyde releasing preservatives, performic acid, peracetic acid, nitrate, and combinations thereof.

The component of the composition can include a pH modifier. The composition can comprise from about 0.1 to 20 wt. %, from about 0.5 to 10 wt. %, or from about 0.5 to 5 wt. % of a pH modifier, based on total weight of the composition. Suitable pH modifiers include, but are not limited to, alkali hydroxides, alkali carbonates, alkali bicarbonates, alkaline earth metal hydroxides, alkaline earth metal carbonates, alkaline earth metal bicarbonates and mixtures or combinations thereof. Exemplary pH modifiers include sodium hydroxide, potassium hydroxide, calcium hydroxide, calcium oxide, sodium carbonate, potassium carbonate, sodium bicarbonate, potassium bicarbonate, magnesium oxide, and magnesium hydroxide.

The component of the composition can include a surfactant. The composition can comprise from about 0.1 to 10 wt. %, from about 0.5 to 5 wt. %, or from about 0.5 to 4 wt. % of a surfactant, based on total weight of the composition. Suitable surfactants include, but are not limited to, anionic surfactants and nonionic surfactants. Anionic surfactants include alkyl aryl sulfonates, olefin sulfonates, paraffin sulfonates, alcohol sulfates, alcohol ether sulfates, alkyl carboxylates and alkyl ether carboxylates, and alkyl and ethoxylated alkyl phosphate esters, and mono and dialkyl sulfosuccinates and sulfosuccinamates. Nonionic surfactants include alcohol alkoxylates, alkylphenol alkoxylates, block copolymers of ethylene, propylene and butylene oxides, alkyl dimethyl amine oxides, alkyl-bis(2-hydroxyethyl) amine oxides, alkyl amidopropyl dimethyl amine oxides, alkylamidopropyl-bis(2-hydroxyethyl) amine oxides, alkyl polyglucosides, polyalkoxylated glycerides, sorbitan esters and polyalkoxylated sorbitan esters, and alkoyl polyethylene glycol esters and diesters. Also included are betaines and sultanes, amphoteric surfactants such as alkyl amphoacetates and amphodiacetates, alkyl amphopropionates and amphodipropionates, and alkyliminodipropionate.

The component of the composition can also include an iron chelator. The iron chelator can be selected from gluconic acid, citric acid, ascorbic acid, tetrakis(hydroxymethyl)phosphonius sulfate (THPS), and combinations thereof.

Antifouling compositions can further include additional functional agents or additives that provide a beneficial property. For example, additional agents or additives can be sequestrants, solubilizers, lubricants, buffers, cleaning agents, rinse aids, preservatives, binders, thickeners or other viscosity modifiers, processing aids, carriers, water-conditioning agents, foam inhibitors or foam generators, threshold agents or systems, aesthetic enhancing agents (i.e., dyes, odorants, perfumes), or other additives suitable for formulation with a corrosion inhibitor composition, and mixtures thereof. Additional agents or additives will vary according to the particular corrosion inhibitor composition being manufactured and its intend use as one skilled in the art will appreciate.

Alternatively, the compositions can not contain any of the additional agents or additives.

Additionally, the antifouling compound can be formulated into a treatment fluid comprising the following components. These formulations include the ranges of the components listed and can optionally include additional agents.

| Component | 1 | 2 | 3 | 4 | 5 | 6 | 7 | 8 | 9 | 10 | 11 | 12 |
|---|---|---|---|---|---|---|---|---|---|---|---|---|
| Antifouling compound | 30-90 | 30-90 | 30-90 | 30-90 | 30-90 | 30-90 | 65-85 | 65-85 | 65-85 | 65-85 | 65-85 | 30-90 |
| Organic solvent | 10-35 | | | | | | 10-35 | | | | | 10-35 |
| Corrosion inhibitor | 0.1-20 | 0.1-20 | | | | | 0.1-20 | 0.1-20 | | | | 0.1-20 |
| Asphaltene inhibitor | 0.1-5 | 0.1-5 | 0.1-5 | 0.1-5 | | | 0.1-5 | 0.1-5 | 0.1-5 | | | 0.1-5 |
| Paraffin inhibitor | | | | | | | | | | | | |
| Scale inhibitor | 1-10 | 1-10 | 1-10 | 1-10 | 1-10 | | 1-10 | 1-10 | 1-10 | 1-10 | | 1-10 |
| Emulsifier | | | | | | | | | | | | |
| Water clarifier | | | | | | | | | | | | |
| Dispersant | | | | | | | | | | | | |
| Emulsion breaker | | | | | | | | | | | | |

-continued

| Component | 1 | 2 | 3 | 4 | 5 | 6 | 7 | 8 | 9 | 10 | 11 | 12 |
|---|---|---|---|---|---|---|---|---|---|---|---|---|
| Gas hydrate inhibitor | | | | | | | | | | | | 0.1-25 |
| Biocide | 0.5-5 | 0.5-5 | 0.5-5 | 0.5-5 | 0.5-5 | 0.5-5 | 0.5-5 | 0.5-5 | 0.5-5 | 0.5-5 | 0.5-5 | |
| pH modifier | | | | | | | | | | | | |
| Surfactant | | | | | | | | | | | | |

| Component | 13 | 14 | 15 | 16 | 17 | 18 | 19 | 20 | 21 | 22 | 23 | 24 |
|---|---|---|---|---|---|---|---|---|---|---|---|---|
| Antifouling compound | 30-90 | 30-90 | 30-90 | 30-90 | 30-90 | 30-90 | 65-85 | 65-85 | 65-85 | 65-85 | 65-85 | 65-85 |
| Organic solvent | | | | | | | | | | | | |
| Corrosion inhibitor | 0.1-20 | 0.1-20 | 0.1-20 | 0.1-20 | 0.1-20 | | 0.1-20 | 0.1-20 | 0.1-20 | 0.1-20 | 0.1-20 | 0.1-20 |
| Asphaltene inhibitor | 0.1-5 | | | | | | 0.1-5 | | | | | |
| Paraffin inhibitor | | | | | | | | | | | | |
| Scale inhibitor | 1-10 | 1-10 | | | 1-10 | | 1-10 | 1-10 | | | | 1-10 |
| Emulsifier | | | | | | | | | | | | |
| Water clarifier | | | | | | | | | | | | |
| Dispersant | | | | | | | | | | | | |
| Emulsion breaker | | | | | | | | | | | | |
| Gas hydrate inhibitor | 0.1-25 | 0.1-25 | 0.1-25 | | | | 0.1-25 | 0.1-25 | 0.1-25 | | 0.1-25 | |
| Biocide | | | | | | 0.5-35 | 0.5-5 | 0.5-5 | 0.5-5 | 0.5-5 | | |
| pH modifier | | | | | | | | | | | | |
| Surfactant | | | | | | | | | | | | |

Unless otherwise indicated, an alkyl group as described herein alone or as part of another group is an optionally substituted linear saturated monovalent hydrocarbon substituent containing from one to sixty carbon atoms and preferably one to thirty carbon atoms in the main chain or eight to thirty carbon atoms in the main chain, or an optionally substituted branched saturated monovalent hydrocarbon substituent containing three to sixty carbon atoms, and preferably eight to thirty carbon atoms in the main chain. Examples of unsubstituted alkyl groups include methyl, ethyl, n-propyl, i-propyl, n-butyl, i-butyl, s-butyl, t-butyl, n-pentyl, i-pentyl, s-pentyl, t-pentyl, and the like.

The term alkoxy as used herein or alone or as part of another group is an —OR group, wherein the R group is a substitued or unsubstituted alkyl group as defined herein.

The terms "aryl" or "ar" as used herein alone or as part of another group (e.g., aralkyl) denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl. The term "aryl" also includes heteroaryl.

The term "substituted" as in "substituted aryl," "substituted alkyl," and the like, means that in the group in question (i.e., the alkyl, aryl or other group that follows the term), at least one hydrogen atom bound to a carbon atom is replaced with one or more substituent groups such as hydroxy (—OH), alkylthio, phosphino, amido (—CON($R_A$)($R_B$), wherein $R_A$ and $R_B$ are independently hydrogen, alkyl, or aryl), amino(—N($R_A$)($R_B$), wherein $R_A$ and $R_B$ are independently hydrogen, alkyl, or aryl), halo (fluoro, chloro, bromo, or iodo), silyl, nitro (—$NO_2$), an ether (—$OR_A$ wherein $R_A$ is alkyl or aryl), an ester (—OC(O)$R_A$ wherein $R_A$ is alkyl or aryl), keto (—C(O)$R_A$ wherein $R_A$ is alkyl or aryl), heterocyclo, and the like. When the term "substituted" introduces a list of possible substituted groups, it is intended that the term apply to every member of that group. That is, the phrase "optionally substituted alkyl or aryl" is to be interpreted as "optionally substituted alkyl or optionally substituted aryl."

The term "heterocyclo," "heterocycle," or "heterocyclyl," as used herein, refers to a monocyclic, bicyclic, or tricyclic group containing 1 to 4 heteroatoms selected from N, O, S(O)$_n$, P(O)$_n$, P$R^z$, NH or N$R^z$, wherein $R^z$ is a suitable substituent. Heterocyclic groups include, but are not limited to, 1,3-oxazetidine, 1,3-diazetidine, 1,3-thiazetidine, oxazolidine, imidazolidine, thiazolidine, 1,3-oxazinane, hexahydropyrimidine, 1,3-thiazinane, 1,3-oxazepane, 1,3-diazepane, 1,3-thiazepane, 1,3-oxazocane, 1,3-diazocane, 1,3-thiazocane. Heterocyclic groups can be unsubstituted or substituted by one or more suitable substituents, preferably 1 to 3 suitable substituents, as defined above.

Having described the invention in detail, it will be apparent that modifications and variations are possible without departing from the scope of the invention defined in the appended claims.

EXAMPLES

The following non-limiting examples are provided to further illustrate the present invention.

Example 1: Synthesis of Novel Surfactant Compositions

The overall synthesis of the surfactants described herein is achieved in two steps (Scheme 1). Acceptor molecule (C) is first prepared by ring opening reaction of an alkyl-epoxide (B) with an aromatic amine or alcohol compound (A). The second step involves oxyalkylation of the acceptor molecule (C) with one or more alkylene oxides (D & E) to afford a series of surfactants (F).

Scheme 1

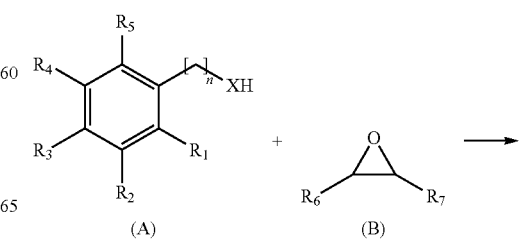

-continued

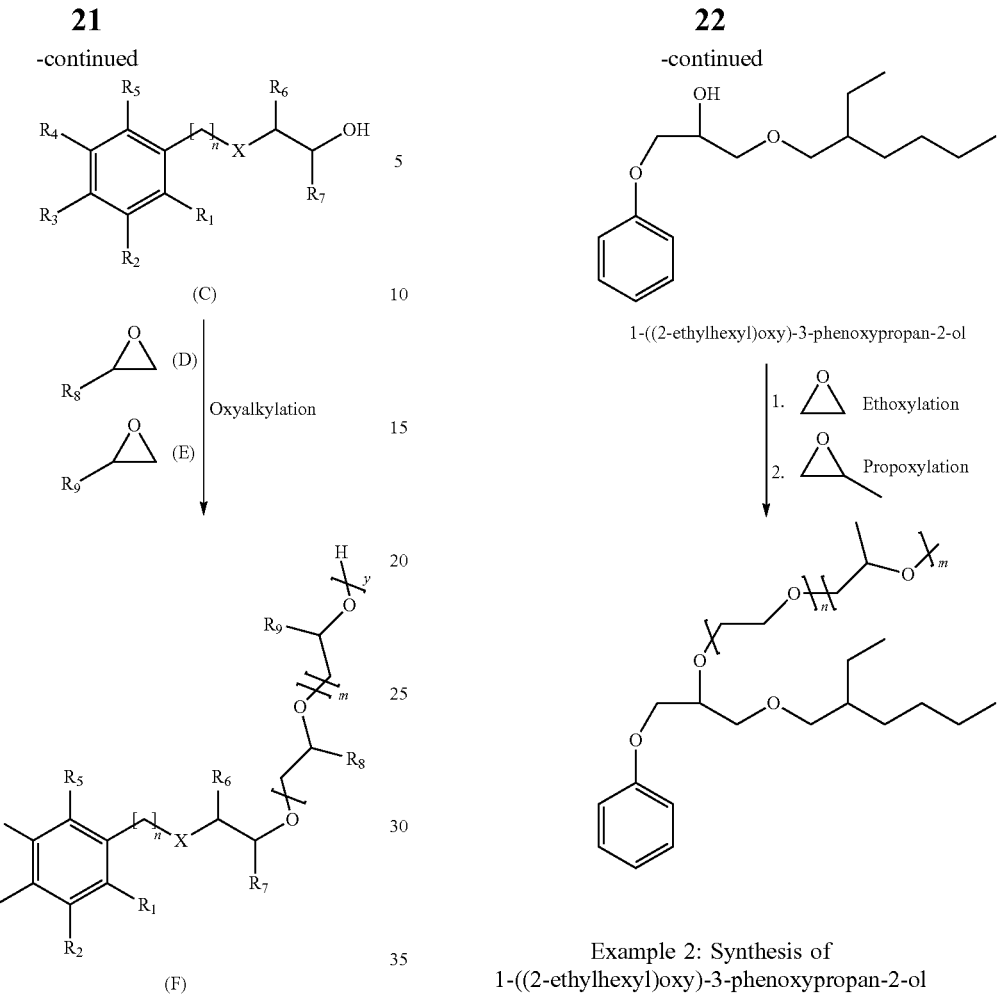

wherein X is —O—, —N(R$_{10}$)—, —OC(O)—, —C(O)O—, —N(R$_{10}$)C(O)—, —C(O)N(R$_{10}$)—, —OC(O)O—, —OC(O)N(R$_{10}$)—, —N(R$_{10}$)C(O)O—, or —N(R$_{10}$)C(O) N(R$_{10}$)—; n is an integer from 0 to 10; R$_6$ and R$_9$ are independently hydrogen, alkyl, or aryl; R$_7$ is alkyl, aryl, or —(CH$_2$)z-O—R$_{11}$, R$_8$ is independently hydrogen, alkyl, or aryl; R$_{10}$ is hydrogen, alkyl, or Z; R$_{11}$ is hydrogen or alkyl; m is independently an integer from 3 to 20; y is independently an integer from 3 to 20; and z is an integer from 1 to 10; and R$_1$, R$_2$, R$_3$, R$_4$, and R$_5$ are independently hydrogen, Z, alkyl, alkoxyl, or two adjacent R groups combine to form a fused ring.

Examples 2-4 disclose the specific synthesis of a series of surfactants which comprise acceptor molecular 1-((2-ethylhexyl)oxy)-3-phenoxypropan-2-ol which is prepared and subsequently both ethoxylated and propoxylated via the following two step process (Scheme 2):

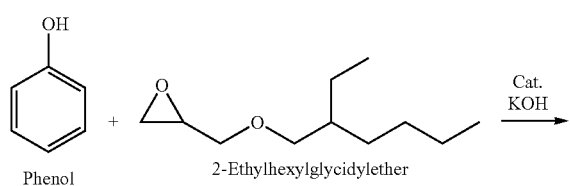

Example 2: Synthesis of 1-((2-ethylhexyl)oxy)-3-phenoxypropan-2-ol

Phenol (100 g, 1.06 mole) and potassium hydroxide (1 g, 0.02 mole) were added to a 500 mL three necked round-bottom flask equipped with temperature probe, condenser, nitrogen inlet and magnetic stir bar and the temperature of the reaction increased to 50° C. 2-Ethylhexylglycidal ether (200 g, 1.06 moles) was then added to the molten phenol under nitrogen blanket. The temperature of the reaction was further increased to 130° C. and stirred for 4 hours or until completion of reaction. Reagents used in the reaction are summarized in Table 1.

TABLE 1

Reagents for synthesis of 1-((2-ethylhexyl)oxy)-3-phenoxypropan-2-ol.

| Reagent | MW (g/mol) | Mass (g) | n (mole) |
|---|---|---|---|
| Phenol | 94.11 | 100 | 1.06 |
| 2-Ethylhexyl glycidyl ether | 186.29 | 200 | 1.06 |
| KOH Pellets | 56.11 | 1 | 0.02 |

Example 3: Addition of Ethylene Oxide to the 1-((2-ethylhexyl)oxy)-3-phenoxypropan-2-ol After catalyzing and dehydrating, 2967.2 g of 1-((2-ethylhexyl)oxy-3-phenoxypropan-2-ol was charged to a oxyalkylation reactor and heated to 125° C. under 10 psi of nitrogen at a stirrer speed of 300 rpm. The ethoxylation reaction was initiated when the acceptor material reached 125° C. The ethylene oxide was charged in step-wise fashion to slowly increase the working pressure range of 55-65 psi during the oxide feed. A slight exotherm was observed. Once the target amount of ethylene oxide, 7477 g (16 mol), was charged to the reactor, the oxide feed was discontinued and the reaction was allowed to proceed for 6 hours at 125° C. The material was then cooled and sampled for testing. Preparation of intermediate with 18 mole of ethylene oxide) was completed through addition of the desired amounts of EO.

Example 4: Addition of Propylene Oxide to the Ethoxylated 1-((2-ethylhexyl)oxy)-3-phenoxypropan-2-ol After catalyzing and dehydrating, ethoxylated 1-((2-ethylhexyl)oxy)-3-phenoxypropan-2-ol was charged to a Parr reactor and heated to 125° C. under 10 psi of nitrogen at a stirrer speed of 300 rpm. The propoxylation reaction was initiated when the acceptor material reached 125° C. The propylene oxide was charged in step-wise fashion to slowly increase the working pressure range of 55-65 psi during the oxide feed. A slight exotherm was observed. Once the target amount of propylene oxide was charged to the reactor, the oxide feed was discontinued and the reaction was allowed to proceed for 6 hours at 125° C. The material was then cooled and sampled for testing. Preparation of intermediates with increasing levels of propylene oxide (4-8 mol PO) was completed through addition of the desired amounts of propylene oxide. The antifouling compounds prepared in this manner are summarized in Table 2.

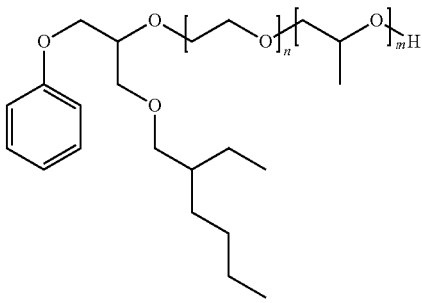

TABLE 2

Antifouling Compounds

| Identifier | Equivalents Ethylene Oxide (n) | Equivalents Propylene Oxide (m) |
|---|---|---|
| 16EO/4PO | 16 | 4 |
| 16EO/5PO | 16 | 5 |
| 16EO/6PO | 16 | 6 |
| 16EO/7PO | 16 | 7 |
| 16EO/8PO | 16 | 8 |
| 18EO/4PO | 18 | 4 |
| 18EO/5PO | 18 | 5 |
| 18EO/6PO | 18 | 6 |
| 18EO/7PO | 18 | 7 |
| 18EO/8PO | 18 | 8 |

Example 5: Aerobic Bacteria Growth and Biofilm Formation Inhibition Assay

The antifouling compounds from Table 2 were tested for inhibition of aerobic bacteria growth and inhibition of biofilm formation. Two different compositions containing single quaternary compounds were also prepared for comparison purposes: sample Quat 1 comprised about 50% by weight bisoctyl dimethyl ammonium chloride (CAS #5538-94-3) and about 5-10% by weight glycerin, and sample Quat 2 comprised about 50% by weight didecyl-dimethyl ammonium chloride (CAS #7173-51-5) and about 10-30% by weight ethanol. The microbial and biofilm inhibition test protocol used was a modified version the MBEC (Minimum Biofilm Eradication Concentration) assay E2799-12 (2011), which is an ASTM (American Society for Testing and Materials) method. Results are shown in Table 3 below.

The bacteria used in this example comprised a mixture of aerobic populations from more than 30 cooling systems in North America. The specific species were not specifically identified. Those bacteria were grown on R2A agar.

The test began with preparation of treated water samples prepared by mixing water (from different water systems or artificial water), known bacterial populations, limited nutrients (16% of medium, 2% (w/w) casitone, 0.8% (w/w) yeast extracts, 4% (v/v) glycerol, 4 ppm $FeCl_3$), and a solution of a treatment chemical. This step generated a series of treated water samples with concentrations of the treatment chemical ranging from 0.8 ppm to 1,000 ppm.

Next, 200 µL of each treated water sample was transferred to a 96 well plate. Six replicates were tested for each concentration of the treatment chemical and for a no treatment chemical control. The plates were placed on a slow rotary shaker and incubated in a humidity-controlled environment at 32-35° C. for 40-48 hours.

After incubation, the bacterial growth in each well of the plate was recorded either visually or by a microplate turbidity reader at 650 nm to determine the minimum bacterial growth inhibition concentration of each treatment chemical.

The fluid on each plate was then gently poured out and 250 ul of dye (350 ppm 2-(4-Iodophenyl)-3-(4-nitrophenyl)-5-phenyltetrazolium chloride (INT) or 2,000 ppm crystal violent (CV)) was added to each well for to stain for biofilms. After 10-15 minutes, the dye was poured out and the wells were gently washed with deionized water until the wash water ran clear. After drying the plates, each well was visually inspected for staining and results were recorded. Alternatively to visual inspection, 300 uL ethanol was added to each well to extract dye from the biofilm, and 200 uL of the ethanol was transferred to a new plate for microtiter plate recording at 590 nm. These results were used to determine the minimum biofilm inhibition concentration of the treatment chemical or composition.

TABLE 3

Aerobic Bacteria Growth and Biofilm Inhibition Assay

| Identifier | Min Planktonic Growth Inhibition (ppm) | Min Biofilm Growth Inhibition | Partial Biofilm Growth Inhibition |
|---|---|---|---|
| Series 1 | | | |
| 16EO/4PO | 500 | 125 | 25 |
| 16EO/5PO | 500 | 125 | 12 |
| 16EO/6PO | 250 | 125 | 12 |
| 16EO/7PO | 500 | 50 | 32 |
| 16EO/8PO | 500 | 50 | 16 |
| Series 2 | | | |
| 18EO/4PO | 250 | 25 | 12 |
| 18EO/5PO | 250 | 25 | 8 |

TABLE 3-continued

Aerobic Bacteria Growth and Biofilm Inhibition Assay

| Identifier | Min Planktonic Growth Inhibition (ppm) | Min Biofilm Growth Inhibition | Partial Biofilm Growth Inhibition |
|---|---|---|---|
| 18EO/6PO | 500 | 16 | 8 |
| 18EO/7PO | 250 | 125 | 50 |
| 18EO/8PO | 500 | 25 | 8 |
| Benchmarking Chemistries | | | |
| Quat 1 | 125 | 25 | 1 |
| Quat 2 | 63 | 45 | 1 |

Example 6: *Pseudomonas* Bacteria Growth and Biofilm Inhibition Assay

The antifouling compounds from Table 1 were tested for inhibition of *Pseudomonas* bacteria growth and inhibition of biofilm formation. Results are shown in Table 4 below. The microbial and biofilm inhibition test protocol used was similar to that of Example 5 above.

The bacteria used in this example comprised a mixture of *Pseudomonas* populations from more than 30 cooling systems in North America. The specific species were not specifically identified. The bacteria were grown on *Pseudomoas* CFC agar.

TABLE 4

*Pseudomonas* Bacteria Growth and Biofilm Inhibition Assay

| Identifier | Min Planktonic Growth Inhibition (ppm) | Min Biofilm Growth Inhibition (ppm) | Partial Biofilm Growth Inhibition (ppm) |
|---|---|---|---|
| Series 1 | | | |
| 16EO/4PO | 500 | 64 | 10 |
| 16EO/5PO | 500 | 125 | 10 |
| 16EO/6PO | 500 | 25 | 5 |
| 16EO/7PO | 250 | 64 | 16 |
| 16EO/8PO | 250 | 64 | 16 |
| Series 2 | | | |
| 18EO/4PO | 500 | 125 | 10 |
| 18EO/5PO | 500 | 32 | 25 |
| 18EO/6PO | 500 | 32 | 25 |
| 18EO/7PO | 500 | 125 | 25 |
| 18EO/8PO | 500 | 125 | 10 |
| Benchmarking Chemistries | | | |
| Quat 1 | 64 | 12 | 1 |
| Quat 2 | 12 | 25 | 1 |

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above methods without departing from the scope of the invention, it is intended that all matter contained in the above description shall be interpreted as illustrative and not in a limiting sense.

The invention claimed is:

1. An antifouling composition comprising an antifouling compound having a structure of Formula 2:

(2)

[Structure of benzene ring with substituents $R_5$, $R_1$, $R_4$, $R_2$, $R_3$, and Z]

wherein

Z has the following structure:

(Z)

[Structure showing chain with $R_6$, $R_9$, X, $R_7$, $R_8$, O, and subscripts p, n, m, terminating in H]

wherein

X is —O— or —N($R_{10}$)—;

p is an integer from 0 to 10;

$R_1$, $R_2$, $R_3$, $R_4$, and $R_5$ are hydrogen;

$R_6$ is hydrogen, alkyl, or aryl;

$R_7$ is —(CH$_2$)z-O—$R_{11}$;

$R_8$ is alkyl;

$R_9$ is hydrogen;

$R_{10}$ is hydrogen or alkyl;

$R_{11}$ is hydrogen or alkyl;

m is an integer from 2 to 20;

n is an integer from 3 to 20; and z is an integer from 1 to 10; and wherein the antifouling composition reduces biofilm growth in a system comprising an aqueous medium.

2. The antifouling composition of claim 1, wherein $R_6$ is hydrogen.

3. The antifouling composition of claim 2, wherein $R_8$ is methyl.

4. The antifouling composition of claim 3, wherein $R_7$ is —(CH$_2$)z-O—$R_{11}$ and z is 1 to 3.

5. The antifouling composition of claim 4, wherein $R_{11}$ is $C_4$ to $C_{22}$ alkyl.

6. The antifouling composition of claim 1, wherein the antifouling compound of Formula 2 has a structure corresponding to

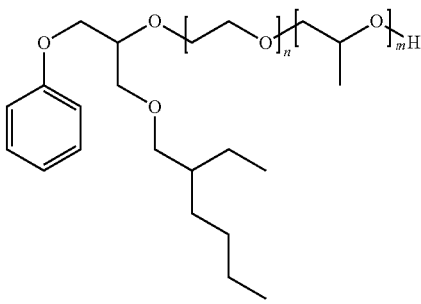

wherein n is an integer from 10 to 20 and m is an integer from 2 to 12.

7. The antifouling composition of claim 6, wherein n is an integer of 16 or 18 and m is an integer from 4 to 8.

8. The antifouling composition of claim 1, wherein the antifouling composition further comprises a corrosion inhibitor and the corrosion inhibitor is an imidazoline compound, a pyridinium compound, or a combination thereof.

9. The antifouling composition of claim 1, wherein the antifouling composition further comprises an additional antifouling agent, wherein the additional antifouling agent is a quaternary compound.

10. The antifouling composition of claim 1, wherein the antifouling composition further comprises a biocide and the biocide is chlorine, hypochlorite, chlorine dioxide, bromine, ozone, hydrogen peroxide, peracetic acid, peroxycarboxylic acid, peroxycarboxylic acid composition, peroxysulfate, glutaraldehyde, dibromonitrilopropionamide, isothiazolone, terbutylazine, polymeric biguanide, methylene bisthiocyanate, tetrakis hydroxymethyl phosphonium sulfate, or a combination thereof.

11. The antifouling composition of claim 1, wherein the antifouling composition further comprises a preservative or an acid and the acid is hydrochloric acid, hydrofluoric acid, citric acid, formic acid, acetic acid, or a mixture thereof.

12. The antifouling composition of claim 1, wherein the antifouling composition further comprises a hydrogen sulfide scavenger and the hydrogen sulfide scavenger is an oxidant, inorganic peroxide, sodium peroxide, chlorine dioxide; a $C_1$-$C_{10}$ aldehyde, formaldehyde, glyoxal, glutaraldehyde, acrolein, methacrolein, a triazine, monoethanolamine triazine, monomethylamine triazine, or a mixture thereof.

13. The antifouling composition of claim 1, wherein the antifouling composition further comprises an asphaltene inhibitor, a paraffin inhibitor, a scale inhibitor, a gas hydrate inhibitor, a pH modifier, an emulsion breaker, a reverse emulsion breaker, a coagulant/flocculant agent, an emulsifier, a water clarifier, a dispersant, an antioxidant, a polymer degradation prevention agent, a permeability modifier, a foaming agent, an antifoaming agent, an emulsifying agent, a carbon dioxide scavenger agent, an oxygen scavenger agent, a gelling agent, a lubricant, a friction reducing agent, a salt, or a mixture thereof.

14. The antifouling composition of claim 1, wherein the antifouling composition has a pH of from about 2 to about 11.

15. A method of controlling microbial fouling in a system comprising an aqueous medium, the method comprising contacting the system with the antifouling composition of claim 1, wherein the antifouling composition reduces bacterial growth or biofilm growth in the system, wherein the aqueous medium comprises fresh water, recycled water, salt water, surface water, produced water, or a mixture thereof.

16. The method of claim 15, wherein the system is a cooling water system, a boiler water system, a petroleum well, a downhole formation, a geothermal well, a mineral washing system, a flotation and benefaction system, a papermaking system, a gas scrubber, an air washer, a continuous casting process in the metallurgical industry, an air conditioning and refrigeration system, a water reclamation system, a water purification system, a membrane filtration system, a food processing system, a clarifier system, a municipal sewage treatment system, a municipal water treatment system, or a potable water system.

\* \* \* \* \*